United States Patent [19]

Doyle et al.

[11] Patent Number: 4,724,329
[45] Date of Patent: Feb. 9, 1988

[54] HIGH EFFICIENCY RADIATION SOURCE FOR INFRARED SPECTROMETRY

[75] Inventors: Walter M. Doyle; John R. Gentile, both of Laguna Beach, Calif.

[73] Assignee: Laser Precision Corporation, Utica, N.Y.

[21] Appl. No.: 539,487

[22] Filed: Oct. 6, 1983

[51] Int. Cl.[4] ............................................. G21G 4/00
[52] U.S. Cl. ............................. 250/504 R; 250/493.1
[58] Field of Search ............... 250/338, 504 R, 495.1, 250/493.1; 356/346

[56] References Cited

U.S. PATENT DOCUMENTS

| | | | |
|---|---|---|---|
| 1,043,009 | 10/1912 | Hoffman | 250/85 |
| 1,859,601 | 5/1932 | Rice | 219/34 |
| 2,088,544 | 7/1937 | Braselton | 250/35 |
| 3,247,383 | 4/1966 | Ulseth et al. | 250/88 |
| 3,316,405 | 4/1967 | Astheimer | 250/85 |
| 3,394,257 | 7/1968 | Moldenhauer | 250/504 |
| 3,458,261 | 7/1969 | Bentley et al. | 250/228 |
| 3,539,811 | 11/1970 | Risgin | 250/85 |
| 4,232,971 | 11/1980 | Suga | 356/402 |
| 4,346,323 | 8/1982 | Hirschfeld | 313/111 |

FOREIGN PATENT DOCUMENTS 853379  7/1981  U.S.S.R. .................... 356/346

OTHER PUBLICATIONS

Buck Scientific, Inc. Cat. E. Norwalk, CT 06855.
"Blackbodies as Sources" Supplied by Applicant pp. 2-16-2-29.

Primary Examiner—Craig E. Church
Assistant Examiner—Richard Hanig
Attorney, Agent, or Firm—Thomas J. Plante

[57] ABSTRACT

The present invention provides a radiation source which essentially matches the throughput radiation of the source to the throughput radiation of the interferometer; and it provides the maximum throughput usable by the interferometer with a minimum use of power at the source. The infrared source in this invention combines a radiating element having the optimum area with a hollow, inwardly-reflecting sphere, whose center is at the radiating element and whose exterior has a single aperture which causes radiation to fill the entrance field of view of the spectrometer.

6 Claims, 7 Drawing Figures

HIGH EFFICIENCY RADIATION SOURCE FOR INFRARED SPECTROMETRY

BACKGROUND OF THE INVENTION

This invention relates to radiation sources for infrared (IR) spectrometry. In general, it is concerned with providing maximum radiation throughput in an interferometer spectrometer, using the minimum amount of power at the radiation source.

Infrared radiation sources for interferometer spectrometers have generally been either globars, which are rods heated by electric current, or coated electrical coils, such as those supplied by Buck Scientific.

The globar is described on page 2-27 of the Infrared Handbook as "a rod of bonded silicon carbide usually capped with metallic caps which serve as electrodes for the conduction of current through the globar", causing it to heat, "yielding radiation at a temperature above 1000° C.". While a globar has a fairly good emissivity throughout the IR region, its power consumption is high (e.g., 200 watts), requiring that its mounting structure be water cooled both to limit heating of the instrument and to preserve the metallic electrodes. Thus, both the structure and its power consumption are costly.

Ceramic coated coilforms, such as those supplied by Buck Scientific, are small diameter, relatively long coils, usually placed inside an insulating housing. They have a lower power consumption (e.g., 42 watts) than globars; and they can be air-cooled, rather than water-cooled. However, the coilform radiation source has several drawbacks, including (a) possible effects on instrument operation due to radiated heat, (b) the requirement for a flow of outside air, and (c) the requirement for a special electrical power supply.

In general, the power sources used in interferometer spectrometers have not been well-designed for that use, and have caused significant waste of power and various accompanying disadvantages.

SUMMARY OF THE INVENTION

The present invention provides a radiation source which essentially matches the throughput radiation of the source to the throughput radiation of the interferometer; and it provides the maximum throughput usable by the interferometer with a minimum use of power at the source.

The infrared source in this invention combines a radiating element having the optimum area with a hollow, inwardly-reflecting sphere, whose center is at the radiating element and whose exterior has a single aperture which causes radiation to fill the entrance field of view of the spectrometer. The reflections from the sphere concentrate the radiation at the radiating element, and the cone angle of radiation entering the interferometer is determined by the radius of the sphere and the size of its aperture. By providing a usable source throughput which is not substantially larger than the usable interferometer throughput, source efficiency is very significantly improved.

DETAILED DESCRIPTION OF SPECIFIC EMBODIMENTS

Figure 1:
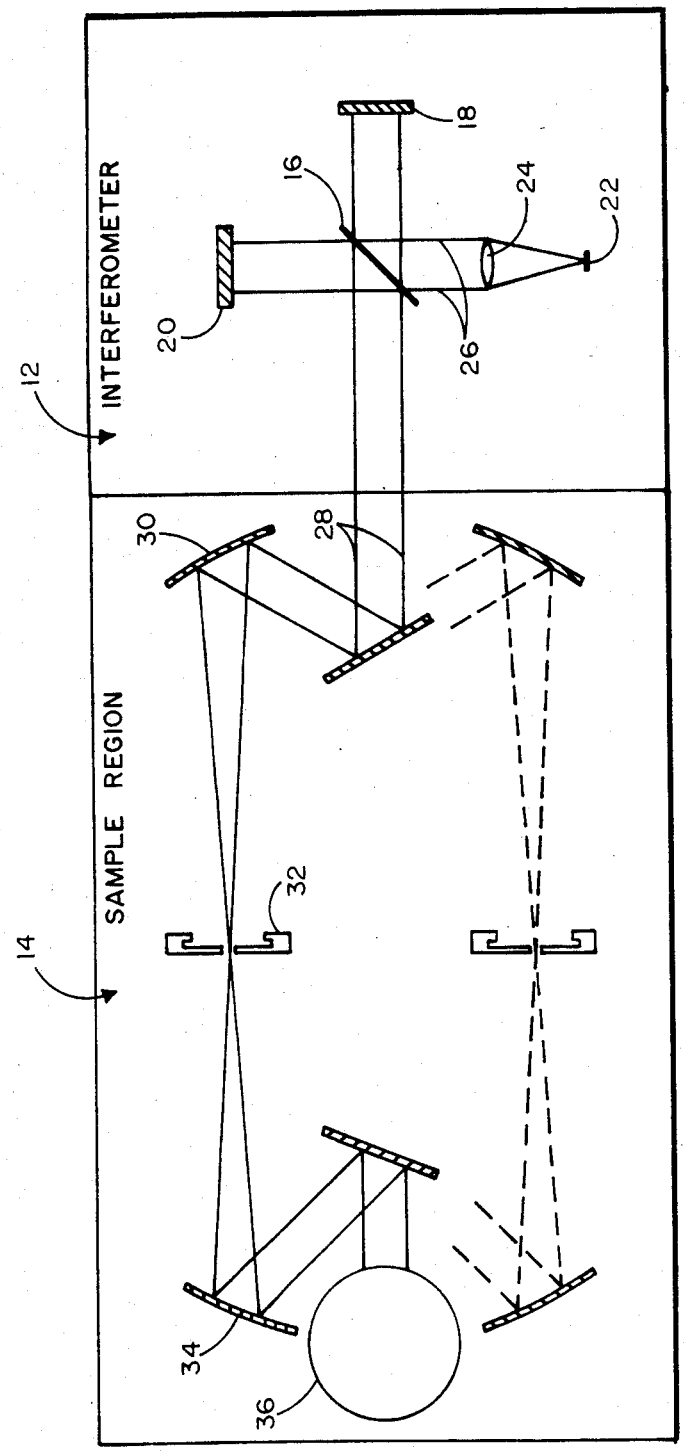
FIG. 1 is a diagrammatic showing of a spectrometer incorporating an interferometer.

FIG. 1 shows a spectrometer having an interferometer region 12 and a sample region 14. A simple form of interferometer is used for illustration of the invention, the interferometer comprising a beamsplitter 16 and two flat mirrors 18 and 20, each at the end of one interferometer arm. The beamsplitter 16 reflects part (preferably 50%) of the radiation to mirror 18 and transmits the rest of the radiation to mirror 20. One of the mirrors is movable toward and away from the beamsplitter, for the purpose of varying the relative lengths of the radiation paths in the two arms.

Radiation entering the interferometer is supplied by a source 22 and shaped by collecting/collimating optics 24 to provide a collimated beam 26 entering the interferometer. A collimated beam 28, representing the recombined beams reflected by the two mirrors 18 and 20, enters the sample chamber 14, and is focused by suitable optics 30 on a sample held by sample holder 32. The post-sample beam is directed by suitable optics 34 to a detector 36.

In providing a radiation source, two goals are important: (a) the interferometer should have the maximum usable radiation throughput; and (b) the energy of the source should not be wasted in dissipation of energy which does not contribute to interferometer throughput. In other words, the guiding principle in combining a radiation source with an interferometer is conservation of throughput.

Figure 2:
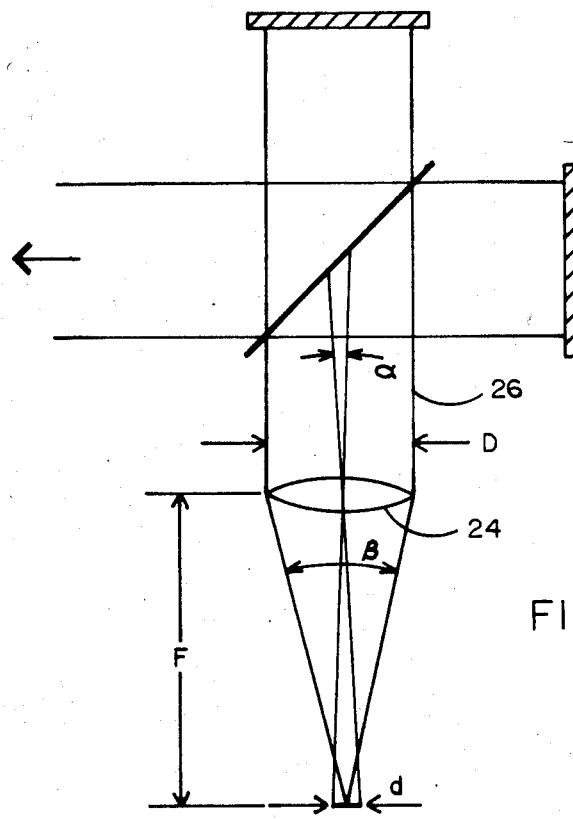
FIG. 2 is a simplified showing of the entrance radiation geometry of an interferometer.

The spatial distribution of radiation which is usable in a Michelson interferometer is determined by: (a) the interferometer aperture, usually a function of the mirror or beamsplitter diameter; and (b) the interferometer field of view (FOV), which is determined by coherence considerations, and which depends on instrument resolution and on the shortest wavelength to be measured. In FIG. 2, the interferometer aperture is represented by collimated beam 26 of circular cross-section having a diameter D. Radiation outside the area represented by diameter D does not contribute to interferometer throughput. The field of view shown in FIG. 2 is the angle indicated by the alpha symbol.

The values of D and of alpha, which determine the maximum usable interferometer throughput, should also be used to determine the radiation propagating characteristics of the source. Assume that: (a) the source 22 has a usable propagating area of diameter d; (b) the usable angle of radiation propagation from the source is represented by beta; and (c) the optical element 24 has a focal length F. Then:

$$\text{beta} = 2 \text{ arc tan } \tfrac{1}{2} \times D/F \tag{1}$$

$$d = 2F \times \tan \text{alpha}/2 \tag{2}$$

Using these equations, and typical values in a practical FTIR (Fourier Transform infrared) spectrometer of D=1 inch, alpha=3.7° and F=2 inches, it can be determined that the value of beta should be approximately 28°, and the value of d should be approximately 3.3 millimeters. These values provide a matching of source throughput to interferometer throughput. Larger values for the source throughput will represent unusable, and therefore wasted, energy.

Figure 3:
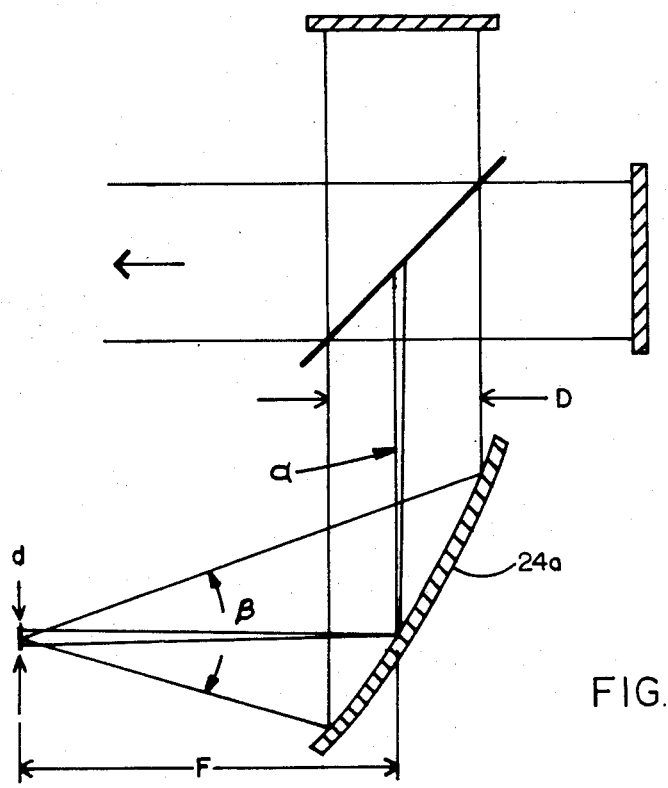
FIG. 3 is a modified version of FIG. 2, showing the entrance radiation geometry of a more complex optical system, of the type used in commercial spectrometers.

FIG. 3 shows a paraboloid reflector 24a as the optical element which collects the source radiation, and outputs the collimated interferometer beam in a commercially practical interferometer. The values alpha, beta, D, d, and F are indicated by letters and symbols in the figure.

Essentially, it is desirable that the size of the source (i.e., diameter d) be as small as feasible; but it still must fill (preferably slightly overfill) the throughput area of the interferometer. On the other hand, if the source is too small, the appropriate focal length (F) of the collecting/collimating optics (24 or 24a) would be so small as to be relatively susceptible to optical aberrations. The field of view (solid angle alpha), as previously stated, has been determined based on interferometer design decisions concerning resolution (wave number) of the instrument and its maximum frequency (wave number). The focal length (F) preferably should be approximately 1.5 to 2.0 times the diameter (D) of the interferometer beam. The usable collecting angle (beta) of the collecting/collimating optics (24 or 24a) is determined by the focal length (F) of the optics and by the diameter (D) of the interferometer beam.

It, therefore, appears that dimensions of the source diameter d and of the angle beta substantially larger than those determined in the manner described will be wasteful of source energy. In other words, the source energy should be emitted from a source area (diameter d) not substantially larger than that determined by equation (2); and its solid angle of propagation (beta) from the source to the collecting optics (24 or 24a) should not be substantially larger than that determined by equation (1).

Figure 4:
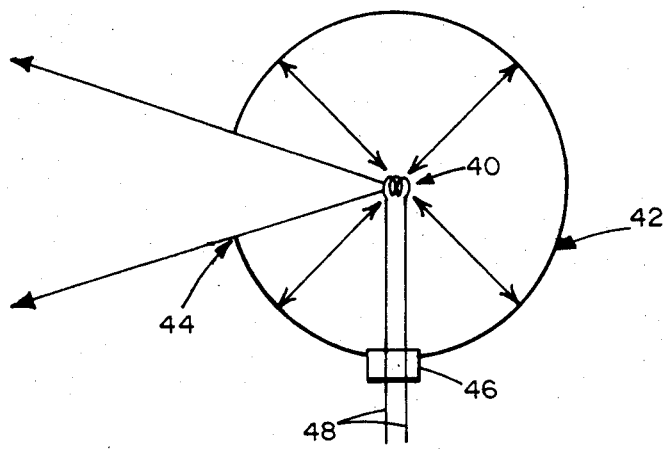
FIG. 4 is a diagrammatic view of the improved radiation source which provides the significant benefits of the present invention.

FIG. 4 shows the improved radiation source which provides the effective dimensions for maximum source efficiency. The source in FIG. 4 is, in effect, the combination of a radiation element 40, and a hollow sphere 42 having an inwardly reflecting-surface, at the center of which element 40 is located. The arrows illustrate paths followed by rays from the element 40. All rays, as shown, are reflected from the wall of sphere 42 back to element 40, except those which pass through an aperture 44 in the side of the sphere and enter the interferometer, filling its entrance field of view. The sphere surface is completely reflecting except for the aperture 44 and a small insulating area 46 required for entrance of electrical leads 48 connected to the radiation source element 40, which is a heated wire coil.

The imaging properties of the hollow inwardly-reflecting sphere 42 are such that the source element 40 located at the center of the sphere will be imaged back on itself, i.e., radiation originating from the source and striking the inner surface of the sphere will be reflected back to the source 40. Since the source is assumed to have a reasonably high emissivity, e.g., 0.8, most of the radiation which returns will be reabsorbed, thereby increasing its temperature. If the inner surface of the sphere 42 were a perfect reflector (emissivity=0), the radiation would be reflected back and forth until all of it was either reabsorbed by the source 40, had exited through the aperture 44, or had struck the wire insulator 46. In this case the sphere would remain cool, and little energy would be wasted. In practice, the sphere coating will have an emissivity of about 0.04 (96% reflecting), so the process will still be reasonably effective.

A convenient material to form sphere 40 is coated aluminum. Because of the tendency of the aluminum to oxidize, a suitable reflecting coating should be used, preferably gold.

There are at least three major practical benefits resulting from the reflection by sphere 42 back to the source element 40:

(1) The reheating, or enhanced heating, of source element 40 by the reflected radiation permits the desired temperature of source 40 to be obtained with a greatly reduced power input.

Figure 5:
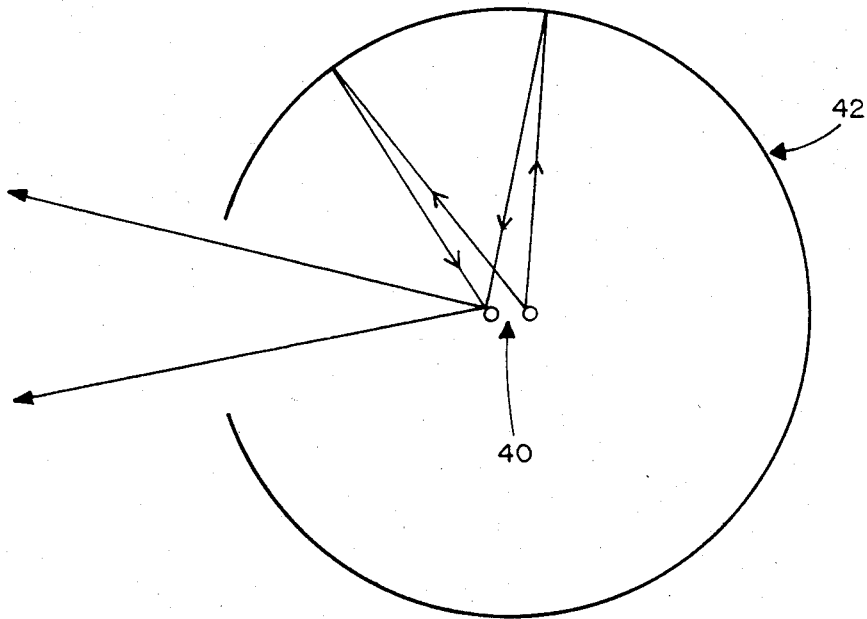
FIG. 5 is a diagrammatic view using exaggerated dimensions of the radiating element for the purpose of further illustrating one of the advantages of the present invention.

(2) There is an enhancement of the apparent source emissivity. FIG. 5 is an enlarged view showing a cross-section of one loop of the coiled wire source 40. Since the two parts of the loop shown lie on opposite sides of the center of the sphere, one part will be imaged on the other. In fact, after several reflections, each part of the coil will seem to be flooded by radiation from almost all directions. The result will be that, for some surface areas of the coil, reflected radiation will be added to the emitted radiation and directed toward the spectrometer aperture. This will make the coil emissivity appear to be greater than it actually is.

(3) The surface of the source coil 40 will appear to be continuous. The wire coil itself will not necessarily present a continuous source surface, but may actually have gaps between the windings. After a few reflections, these gaps will be almost completely filled by radiation reflected from the rear wall of the sphere and imaged in the source region. In other words, there is an improved effective uniformity of the surface area of the source.

The optimum size of the hollow reflecting sphere 42 depends on certain design considerations. Its diameter should be large compared to the dimensions of the coil 40, so as to minimize spherical aberrations, which would tend to degrade the imaging of the coil on itself. In addition, a large diameter sphere will minimize the loss due to the fixed size insulator 46. On the other hand, the size of sphere 42 is limited by the available space in the instrument, and by the constraints on the location of the collimating optics 24 at the input of the interferometer.

Once the diameter of sphere 42 has been selected, the size of aperture 44 should be such that the solid cone angle of radiation from source element 40 creates a radiation cone area at the collecting/collimating optical element (24 or 24a) which is substantially equal to (preferably slightly larger than) the cross-sectional area of the collimated throughput beam 26. Thus the source throughput and the interferometer throughput are matched, minimizing waste of source energy.

Figure 6:
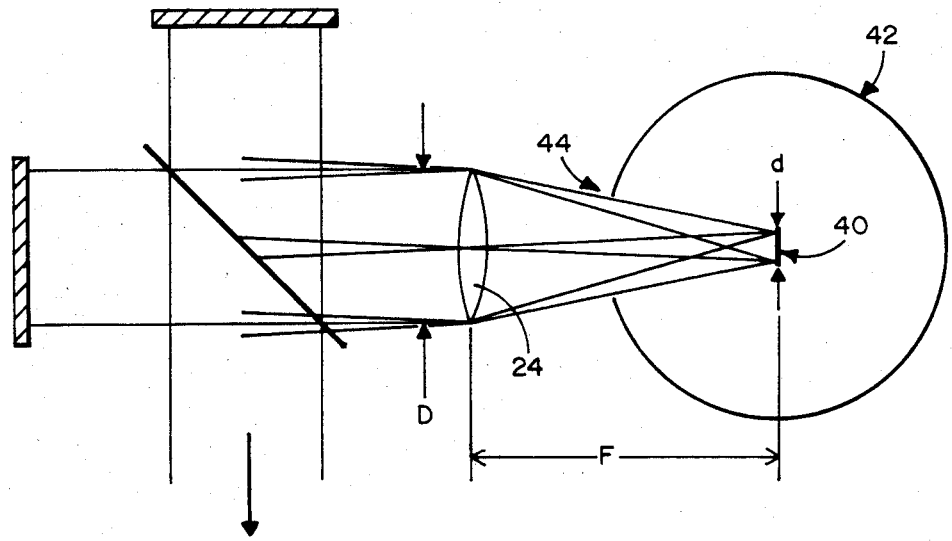
FIG. 6 is a diagrammatic view showing the relationship between the throughput of the interferometer and the throughput of the radiation source.

The extreme ray lines shown in FIG. 6 determine the minimize size of aperture 44, i.e., the ray lines drawn from the periphery of source element 40 to the periphery of the collimated beam 26 at optical element 24 or 24a. The aperture 44 should not be substantially larger than the area required for transmission of such extreme rays, because a larger aperture would permit the escape of radiation from the source which is unusable in the interferometer. In effect, the size of aperture 44 is substantially determined by, but slightly larger than, the vertical cross-section of the cone subtended by the angle beta, which is the solid cone angle created by diverging lines extending from the center of radiation source 40 to the periphery of collimated beam 26. By drawing extreme ray lines (as shown in FIG. 6) from the periphery of source 40 (diameter d) to the periphery of the effective interferometer beam 26 (diameter D), the maximum usable area of aperture 44 is determined.

The conservation of throughput, i.e., the matching of source throughput to interferometer throughput, has the three-fold advantage previously discussed. (1) It reduces the electrical power input required to obtain the desired source temperature (say 1300° K.), or conversely, it increases the source temperature obtained by a given power input. (2) It increases the apparent emissivity of the source. (3) It increases the effective area of the source.

The net result is a radical improvement in source efficiency, by approximately a 5 to 1 ratio over previous FTIR sources. Because the reflecting characteristics are inherently imperfect, and because there are other losses inherent in any such system, it is estimated that about 50% of the available power is converted into interferometer throughput. This compares with previous systems in which the estimated power convertion to throughput is in the neighborhood of 10%.

Figure 7:
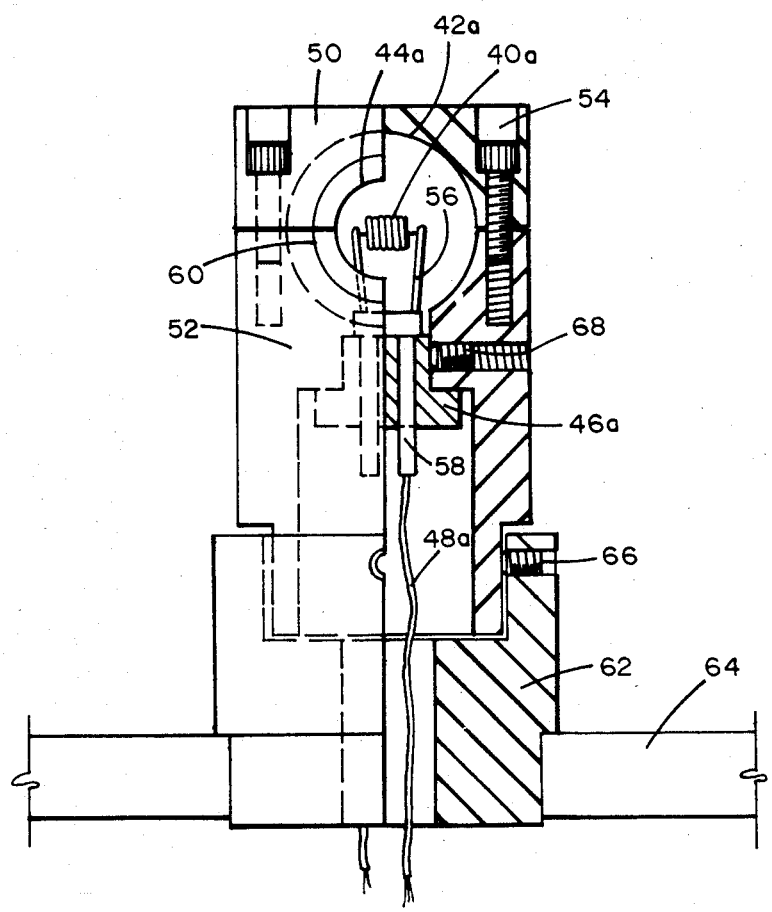
FIG. 7 is a part-outline, part-sectional view of a practical embodiment of the improved radiation source.

FIG. 7 shows a practical embodiment of the improved radiation source. The hollow reflecting sphere 42a is provided by spherical recesses in upper and lower housing elements 50 and 52, which are secured together by suitable fastening members 54. The coil which constitutes radiation source element 40a is supported at the center of the sphere by vertically-extending terminals 56 which are connected by connector pins 58 exteding through insulating socket 46a to electrical leads 48a.

The size of aperture 44a at the interior surface of housing elements 50 and 52 controls the size of the radiation cone which exits the sphere. The aperture is flared to provide a larger diameter opening 60 at the exterior surface of elements 50 and 52.

The lower element 52 may be supported by an adaptor element 62, which is carried on a mounting flange 64. Set screws 66 and 68 are provided to prevent undesired rotation of lower housing element 52 and socket 46, respectively. The orientation of the coil radiation element 40a is preferably such that the axis of the coil is perpendicular to the radiation exiting through aperture 44a.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. A radiation source for use in an interferometer spectrometer, the maximum usable area of source radiation seen by the interferometer and the maximum usable angle of source emission being determined by (a) the interferometer collimated aperture area (diameter D), (b) the interferometer field of view (angle alpha) the focal length (F), of the collimating optics between the source and interferometer; said radiation source comprising:

a hollow enclosure having an inwardly-facing spherical reflecting surface;

a radiation element located at the center of said spherical reflecting surface, said element having an effective radiating area not substantially larger than that defined by the interferometer field of view and the focal length of the collimating optics;

said spherical reflecting surface having an interferometer-illuminating aperture at one side thereof whose area is not substantially larger than that defined by lines extending form the periphery of the effective area of the radiation element to the periphery of the interferometer aperture area at the collimating optics; wherein, the value of angle beta, the usable collecting angle of the collimating optics has the following relationship:

beta = 2 arc tan ½ × D/F; and the value of d, the usable diameter of the radiation source has the following relationship:

d = 2F tan alpha/2; and the diameter of the interferometer-facing aperture in the inwardly-reflecting sphere being substantially the minimum size determined by beta, d, and the diameter of the sphere, in order to match the throughputs of the radiation source and the interferometer.

2. An interferometer spectrometer comprising: collimating optics having a focal distance F which receives entering cone-shaped radiation having an angle beta and provides a collimated output beam having a cross-sectional area which fills the available throughput area of the interferometer having diameter D; the value of beta being:

beta = 2 arc tan ½ × D/F;

a radiation source having an effective radiating area of diamter d, facing toward the collimating optics which area has a periphery determined by the field of view, angle alpha of the interferometer and the focal length, F of the collimating optics, the value of d being:

d = 2 F tan alpha/2; a hollow inwardly-reflecting sphere so located as to have the radiation source at its center, thereby reflecting radiation from the source back on the source;

said sphere having an aperture between the source and the collimating axis, the periphery and thus the area of the aperture being substantially determined by straight lines connecting the periphery of the source to the periphery of the collimated interferometer beam provided by the collimating optics; and the diameter of the interferometer-facing aperture in the inwardly-reflecting sphere being substantially the minimum size determined by beta, d, and the diameter of the sphere, in order to match the throughputs of the radiation source and the interferometer.

3. The interferometer spectrometer of claim 2 wherein the source has an emissivity of less than 1.0, and the reflection of radiation by the sphere back to the source causes an increase in the apparent emissivity of the source.

4. The interferometer spectrometer of claim 2 wherein the source is an electric coil the uniformity of whose effective radiating area is increased by the reflection from the sphere back to the source.

5. The radiation source of claim 1 wherein the radiation element has relatively high emissivity and relatively low reflectivity.

6. The interferometer spectrometer of claim 2 wherein the radiation source has relatively high emissivity and relatively low reflectivity.

* * * * *